US011045622B1

(12) United States Patent
Johnson et al.

(10) Patent No.: US 11,045,622 B1
(45) Date of Patent: Jun. 29, 2021

(54) SHOULDER-WORN DIFFUSER

(71) Applicants: James M. Johnson, Little Rock, AR (US); Joel Johnson, Little Rock, AR (US)

(72) Inventors: James M. Johnson, Little Rock, AR (US); Joel Johnson, Little Rock, AR (US)

(*) Notice: Subject to any disclaimer, the term of this patent is extended or adjusted under 35 U.S.C. 154(b) by 0 days.

(21) Appl. No.: 16/900,867

(22) Filed: Jun. 12, 2020

(51) Int. Cl.
*A61M 21/02* (2006.01)
*A61L 9/03* (2006.01)
*A61M 11/04* (2006.01)
*A61M 11/00* (2006.01)
*A61L 9/14* (2006.01)
*H04M 1/72409* (2021.01)
*A61M 21/00* (2006.01)

(52) U.S. Cl.
CPC ............ *A61M 21/02* (2013.01); *A61L 9/032* (2013.01); *A61L 9/14* (2013.01); *A61M 11/005* (2013.01); *A61M 11/042* (2014.02); *H04M 1/72409* (2021.01); *A61L 2209/11* (2013.01); *A61L 2209/132* (2013.01); *A61L 2209/135* (2013.01); *A61L 2209/14* (2013.01); *A61M 2021/0016* (2013.01); *A61M 2205/3592* (2013.01); *A61M 2205/3653* (2013.01); *A61M 2205/502* (2013.01); *A61M 2205/75* (2013.01); *A61M 2205/8206* (2013.01); *A61M 2230/06* (2013.01); *A61M 2230/20* (2013.01); *A61M 2230/50* (2013.01)

(58) Field of Classification Search
CPC ............ A61M 15/002; A61M 15/0028; A61M 15/003; A61M 15/0031; A61M 15/0085; A61M 11/002; A61M 11/02; A61M 11/005; A61L 9/00; A61L 9/032; A61L 9/14; A61K 2209/132
See application file for complete search history.

(56) References Cited

U.S. PATENT DOCUMENTS

| 9,724,483 B2 * | 8/2017 | Hyde ..................... A61B 5/411 |
| 10,537,754 B1 * | 1/2020 | Vukelja ............. A61B 5/14551 |
| 2006/0065986 A1 * | 3/2006 | Morie ..................... A61K 8/02 |
| | | 261/26 |

(Continued)

FOREIGN PATENT DOCUMENTS

WO WO-2015140776 A1 * 9/2015 ............... A62B 7/10

*Primary Examiner* — Margaret M Luarca
(74) *Attorney, Agent, or Firm* — QuickPatents, LLC; Kevin Prince

(57) ABSTRACT

A device for diffusing a liquid into a vapor proximate a face of a person comprises a U-shaped enclosure that has two legs connected with a back portion for resting on shoulders of the person around a neck of the person. A top side of the enclosure has at least one diffusion port. A control circuit disposed within the interior space of the enclosure includes a controller, at least one user interface, a power source, and a diffusion mechanism connecting a reservoir containing the liquid with the at least one diffusion port. Wherein the person has a smart phone running a software application, the controller may further include a processor, a non-volatile memory, and a wireless network module adapted to wirelessly communicate with the software application running on the smart phone to control a diffusion rate, an on/off status of the device, and a timer.

17 Claims, 3 Drawing Sheets

(56) References Cited

U.S. PATENT DOCUMENTS

| | | | |
|---|---|---|---|
| 2012/0174922 A1* | 7/2012 | Virr | A62B 23/025 |
| | | | 128/203.12 |
| 2016/0114069 A1* | 4/2016 | Huynh | A01M 1/2072 |
| | | | 261/142 |
| 2017/0055904 A1* | 3/2017 | Iizuka | A61B 5/14551 |
| 2018/0056013 A1* | 3/2018 | Knowles | A61M 21/02 |

* cited by examiner

SHOULDER-WORN DIFFUSER

CROSS-REFERENCE TO RELATED APPLICATIONS

Not Applicable.

STATEMENT REGARDING FEDERALLY SPONSORED RESEARCH AND DEVELOPMENT

Not Applicable.

FIELD OF THE INVENTION

This invention relates to air sanitizing, and more particularly to a shoulder-worn air filter and sanitizer.

BACKGROUND

Before the Covid-19 pandemic, people would engage in common activities such as attending school and church, going shopping, and eating out at a restaurant routinely without thinking about dangerous viruses that may be lurking in air surrounding the person's face. With particularly infectious pathogens, it would be advantageous to be able to sterilize the air around one's face while out in public. Heretofore, however, no prior art device provides such a benefit. Further, even when not in public, there are times when a person desires aromatherapy with essential oils or other compositions.

Therefore, there is a need for a device that can diffuse a liquid such as an essential oil or an anti-viral compositions proximate a person's face. Such a needed device would be comfortable to wear on the person's shoulders for an extended period of time, and would create a curtain of sanitized or conditioned air or aromatherapy in front of the person's nose and mouth. Such a needed invention would interface with a smart phone software application to allow the person to easily control the functions of the device. The present invention accomplishes these objectives.

SUMMARY OF THE INVENTION

The present device is a device for diffusing a liquid into a vapor proximate a face of a person having a neck and shoulders. Such a liquid may contain medicine such as albuterol sulfate for treating asthma, essential oils, anti-bacterial or anti-viral compositions, or the like. The device comprises a generally U-shaped enclosure that has a top side, a bottom side, an inside peripheral edge, and an outside peripheral edge. The enclosure includes two legs connected with a back portion for resting on the shoulders of the person around the person's neck. The bottom side of the enclosure is shaped to conform to a curvature of the person's shoulders, and may include a cushioning pad for comfort of the person's shoulders.

The top side of the enclosure has at least one diffusion port in fluid communication with an interior space of the enclosure. Preferably the enclosure includes exactly two of the diffusion ports, one on the top surface of each leg of the enclosure. Each diffusion port preferably includes adjustable baffles for selectively directing the flow of the vapor and air from a diffusion mechanism.

A control circuit is fixed at least partially within the interior space of the enclosure and includes a controller, at least one user interface traversing the enclosure, a power source, and the diffusion mechanism connecting a reservoir that is adapted to contain the liquid with the at least one diffusion port.

In some embodiments the diffusion mechanism includes an electrically heated vaporizer for vaporizing the liquid into the vapor. Alternately, or additionally, the diffusion mechanism may include a fan for blowing air over an absorbent material that is in fluid communication with the reservoir and is infused with the liquid. In such an embodiment, at least one air inlet port traversed the enclosure, preferably at the outside peripheral edge of the back portion of the enclosure, to allow air to enter the interior space of the enclosure, pass over the absorbent material, and exit the enclosure as the vapor through the at least one diffusion port. Each of the at least one inlet ports may include a removable air filter. Alternately the diffusion mechanism includes an ultrasonic atomizer adapted to atomize the liquid.

In a preferred embodiment of the invention, the person has a smart phone running a software application. The controller in such an embodiment further includes a processor, a non-volatile memory, and a wireless network module adapted to wirelessly communicate with the software application running on the smart phone, such as through a Bluetooth, WiFi, or other wireless protocol. The software application is adapted to control the control circuit to change at least a diffusion rate of the liquid, an on/off state of the diffusion mechanism, and a timer that controls a duration of time that the diffusion mechanism is active. Such a timer may be set for a single duration of time, such as minutes, or set for a repeating duration of time, such as minutes every two hours, for example.

As such, with the enclosure resting on the person's shoulders, the at least one user interface may be actuated to activate the control circuit to diffuse the liquid through the at least one diffusion port proximate the person's face.

The present invention is a device that can diffuse a liquid such as an essential oil or an anti-viral compositions proximate a person's face. The present device is comfortable to wear on the person's shoulders for an extended period of time, and creates a curtain of sanitized or conditioned air or aromatherapy in front of the person's nose and mouth. The present invention can wirelessly interact with a smart phone software application to allow the person to easily control the functions of the device. Other features and advantages of the present invention will become apparent from the following more detailed description, taken in conjunction with the accompanying drawings, which illustrate, by way of example, the principles of the invention.

DESCRIPTION OF THE DRAWINGS

FIG. 1 is a front perspective view of the invention;

FIG. 2 is an alternate perspective view of the invention; and

FIG. 3 is a top plan view of the invention, partially broken away, and further illustrating a smart phone running a software application that wirelessly interfaces with the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
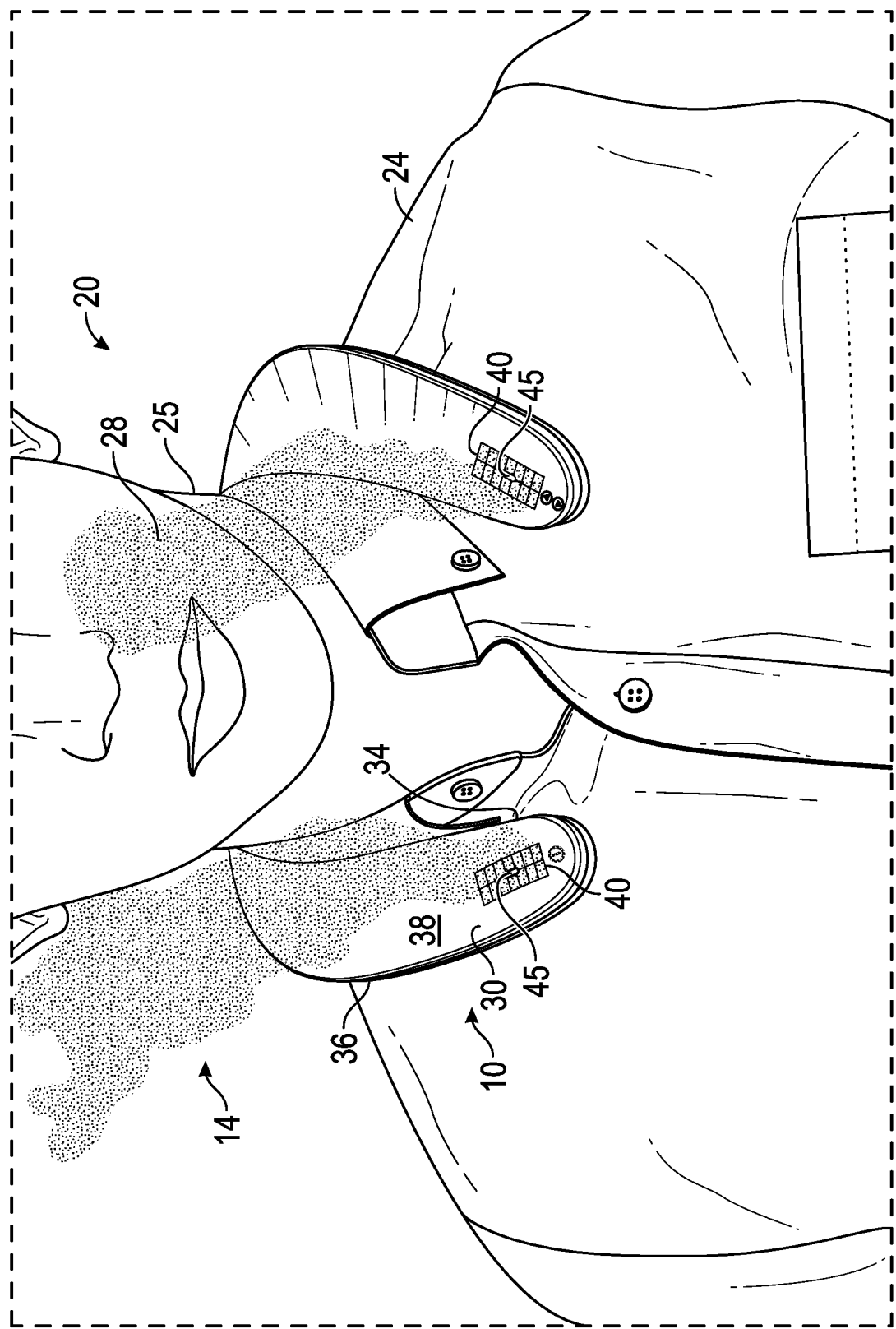
Figure 2:
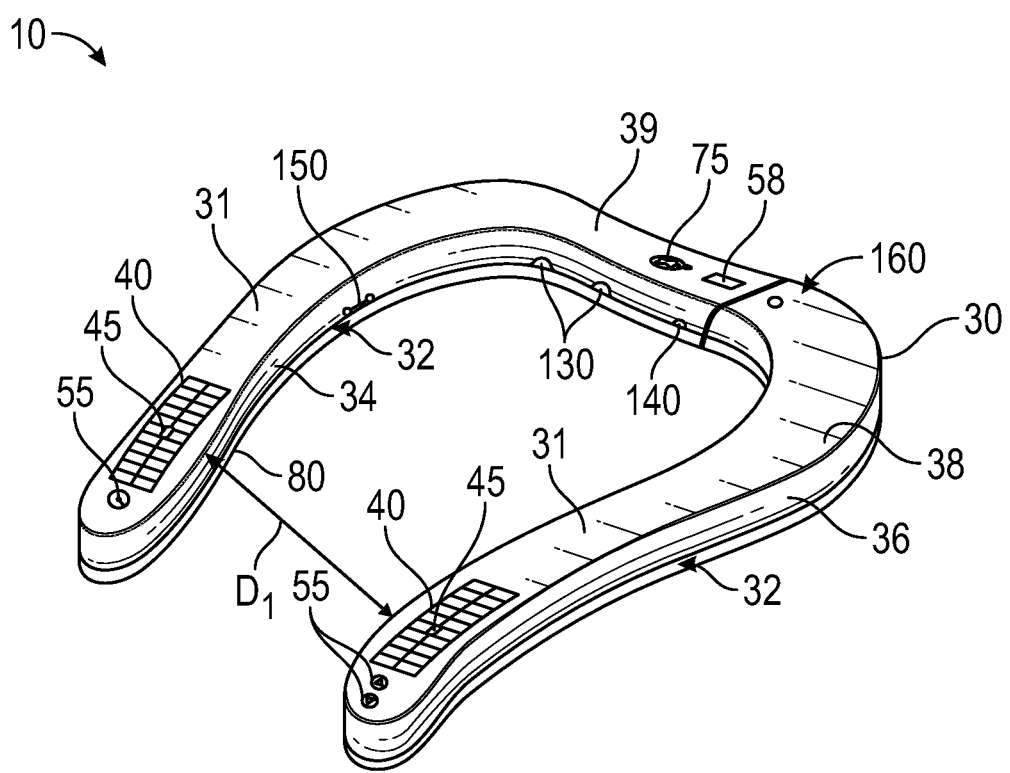
Figure 3:
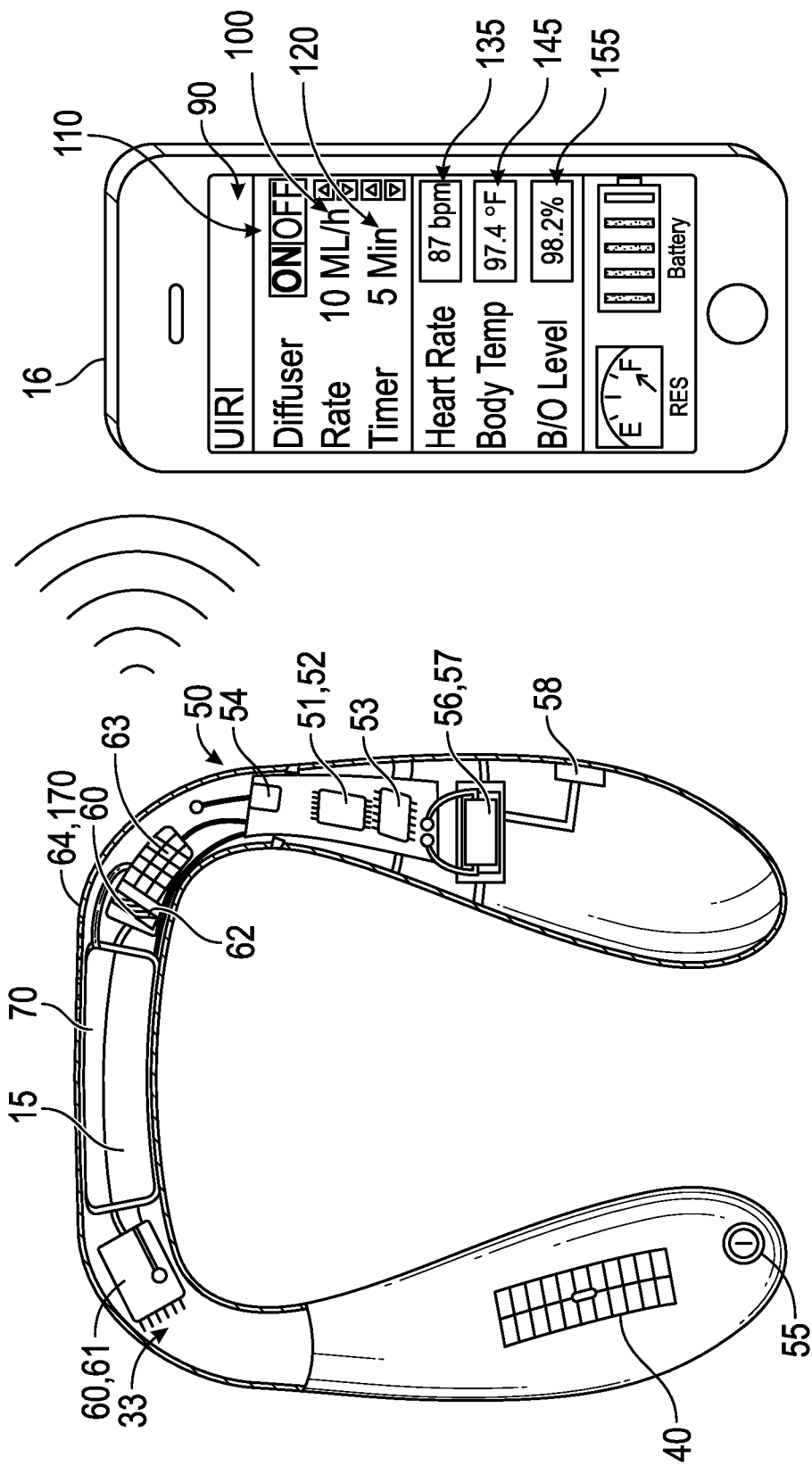

FIGS. 1-3 illustrate a device 10 for diffusing a liquid 15 into a vapor 14 proximate a face 28 of a person 20 having a neck 25 and shoulders 24. Such a liquid may contain medicine such as albuterol sulfate for treating asthma, essential oils, anti-bacterial or anti-viral compositions, or the like.

The device 10 comprises a generally U-shaped enclosure 30 that has a top side 38, a bottom side 32, an inside peripheral edge 34, and an outside peripheral edge 36. The enclosure 30 includes two legs 31 connected with a back portion 39 for resting on the shoulders 24 of the person 20 around the person's neck 25. The bottom side 32 of the enclosure 30 is shaped to conform to a curvature of the person's shoulders 24, and may include a cushioning pad 80 for comfort of the person's shoulders 24. In some embodiments the back portion 39 of the enclosure 30 includes a size adjustment mechanism 160 for allowing the person 20 to selectively adjust a distance D1 between the legs 31 of the enclosure 30 (FIG. 2). Such a size adjustment mechanism 160 may be a telescoping portion 160 as illustrated in FIG. 2, or other size adjustment mechanisms 160 as are known in the art. Preferably the enclosure 30 is rigid and made of plastic or wood, for example.

The top side 38 of the enclosure 30 has at least one diffusion port 40 in fluid communication with an interior space 33 of the enclosure. Preferably the enclosure 30 includes exactly two of the diffusion ports 40, one on the top surface 38 of each leg 31 of the enclosure 30. Each diffusion port 40 preferably includes adjustable baffles 45 for selectively directing the flow of the vapor 14 and air from a diffusion mechanism 60.

A control circuit 50 is fixed at least partially within the interior space 33 of the enclosure 30 and includes a controller 51, at least one user interface 55 traversing the enclosure 30, a power source 56, and the diffusion mechanism 60 connecting a reservoir 70 that is adapted to contain the liquid 15 with the at least one diffusion port 40. Preferably the reservoir 70 includes a filling port 75 traversing the enclosure 30 and is in fluid communication with the reservoir 70, so that the reservoir 70 may be refilled with the liquid 15 when necessary. A gauge (not shown) within the reservoir may be included for indicating a liquid level within the reservoir 70.

Preferably the power source 56 is a rechargeable battery 57. In such an embodiment a battery recharging port 58 traverses the enclosure 30 and is electrically connected with the rechargeable battery 57, such that the rechargeable battery can be recharged by connecting an outside power source (not shown) to the battery recharging port 58. The battery recharging port 58 is preferably a USB or micro-USB port, as is known in the art.

In some embodiments the diffusion mechanism 60 includes an electrically heated vaporizer 61 for vaporizing the liquid 15 into the vapor 14. Alternately, or additionally, the diffusion mechanism 60 may include a fan 62 for blowing air over an absorbent material 63 that is in fluid communication with the reservoir 70 and is infused with the liquid 15. In such an embodiment, at least one air inlet port 64 traverses the enclosure 30, preferably at the outside peripheral edge 36 of the back portion 39 of the enclosure 30, to allow air to enter the interior space 33 of the enclosure 30, pass over the absorbent material 63, and exit the enclosure 30 as the vapor 14 through the at least one diffusion port 40. Each of the at least one inlet ports 64 may include a removable air filter 170. Alternately the diffusion mechanism 60 includes an ultrasonic atomizer adapted to atomize the liquid 15.

In a preferred embodiment of the invention, the person 20 has a smart phone 16 running a software application 90. The controller 51 in such an embodiment further includes a processor 52, a non-volatile memory 53, and a wireless network module 54 adapted to wirelessly communicate with the software application 90 running on the smart phone 16, such as through a Bluetooth, WiFi, or other wireless protocol. The software application 90 is adapted to control the control circuit 50 to change at least a diffusion rate 100 of the liquid 15, an on/off state 110 of the diffusion mechanism 60, and a timer 120 that controls a duration of time that the diffusion mechanism 60 is active. Such a timer 120 may be set for a single duration of time, such as 30 minutes, or set for a repeating duration of time, such as 30 minutes every two hours, for example.

In the preferred embodiment, the device 10 further includes at least two electrodes 130 traversing the enclosure 30 and adapted to make contact with the person's neck 25. The electrodes 130 are electrically connected with the control circuit 50, which is adapted to determine from the electrodes 130 a heart rate 135 of the person 20 and communicate the heart rate 135 to the software application 90 on the smart phone 16.

Similarly, the device 10 may further include a temperature sensor 140 traversing the enclosure 30. The temperature sensor 140 is electrically connected with the control circuit 50 that is adapted to determine from the temperature sensor 140 a body temperature 145 of the person 20 and communicate the body temperature 145 to the software application 90 on the smart phone 16.

Similarly, the device 10 may further include a blood oxygen sensor 150 traversing the enclosure 30. The blood oxygen sensor 150 is electrically connected with the control circuit 50 that is adapted to determine from the blood oxygen sensor 150 a blood oxygen concentration 155 of the person 20 and communicate the blood oxygen concentration 155 to the software application 90 on the smart phone 16.

As such, with the enclosure 30 resting on the person's shoulders 24, the at least one user interface 55 may be actuated to activate the control circuit 50 to diffuse the liquid 15 through the at least one diffusion port 40 proximate the person's face 28.

While a particular form of the invention has been illustrated and described, it will be apparent that various modifications can be made without departing from the spirit and scope of the invention. For example, various diffusing mechanisms 60 may be utilized as are known in the art. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention. The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A device for diffusing a liquid proximate a face of a person having a neck and shoulders, the device comprising:
    a generally U-shaped enclosure having a top side, a bottom side opposing the top side, an inside peripheral edge, and an outside peripheral edge, the enclosure including two legs connected with a back portion, the enclosure adapted for resting on the shoulders of the person around the person's neck, the bottom side of the enclosure shaped to conform to a curvature of the person's shoulders, the top side of the enclosure having at least one diffusion port in fluid communication with an interior space of the enclosure;
    a control circuit fixed at least partially within the interior space of the enclosure and including a controller, at least one user interface traversing the enclosure, a power source, and a diffusion mechanism connecting a reservoir disposed within the interior space of the enclosure with the at least one diffusion port in fluid communication with the interior space of the enclosure, the reservoir being adapted to receive and contain the liquid therein such that, during filling of the reservoir, the liquid is permitted to flow into the reservoir from outside of the reservoir, wherein when the reservoir contains the liquid and the control circuit is activated, the diffusion mechanism diffuses the liquid from the reservoir into the interior space of the enclosure and through the at least one diffusion port of the enclosure;
    whereby with the enclosure resting on the person's shoulders, the at least one user interface may be actuated to activate the control circuit to diffuse the liquid through the at least one diffusion port proximate the person's face.

2. The device of claim 1 wherein the enclosure includes a filling port traversing the enclosure and in fluid communication with the reservoir.

3. The device of claim 1 wherein the bottom side of the enclosure includes a cushioning pad.

4. The device of claim 1 wherein the at least one diffusion port includes exactly two diffusion ports, one diffusion port on the top surface of each leg of the enclosure.

5. The device of claim 1 wherein the at least one diffusion port includes adjustable baffles for selectively directing at least air flow from the diffusion mechanism.

6. The device of claim 1 wherein the diffusion mechanism includes an electrically heated vaporizer.

7. The device of claim 1 wherein the diffusion mechanism includes a fan for blowing air over an absorbent material in fluid communication with the reservoir and infused with the liquid, at least one air inlet port traversing the enclosure to allow air to enter the enclosure, pass over the absorbent material, and exit the enclosure through the at least one diffusion port.

8. The device of claim 7 wherein the at least one inlet port includes a removable air filter.

9. The device of claim 1 wherein the diffusion mechanism includes an ultrasonic atomizer adapted to atomize the liquid.

10. The device of claim 1 wherein the controller further includes a processor, a non-volatile memory, and a wireless network module, the wireless network module adapted to wirelessly communicate with a software application resident and running on a smart phone, the software application adapted to control the control circuit to change at least a diffusion rate of the liquid, an on/off state of the diffusion mechanism, and a timer that controls a duration of time that the diffusion mechanism is active.

11. The device of claim 10 further including at least two electrodes traversing the enclosure and adapted to make contact with the person's neck, the electrodes electrically connected with the control circuit, the control circuit adapted to determine from the electrodes a heart rate of the person and communicate the heart rate to the software application on the smart phone.

12. The device of claim 10 further including a temperature sensor traversing the enclosure and electrically connected with the control circuit, the control circuit adapted to determine from the temperature sensor a body temperature of the person and communicate the body temperature to the software application on the smart phone.

13. The device of claim 10 further including a blood oxygen sensor traversing the enclosure and electrically connected with the control circuit, the control circuit adapted to determine from the blood oxygen sensor a blood oxygen concentration of the person and communicate the blood oxygen concentration to the software application on the smart phone.

14. The device of claim 1 wherein the power source is a rechargeable battery, a battery recharging port traversing the enclosure and electrically connected with the rechargeable battery, whereby the rechargeable battery can be recharged by connecting an outside power source to the battery recharging port.

15. The device of claim 1 wherein the back portion of the enclosure includes a size adjustment mechanism for allowing the person to selectively adjust a distance between the legs of the enclosure.

16. A device for diffusing a liquid proximate a face of a person having a neck and shoulders, the device comprising:
- a generally U-shaped enclosure having a top side, a bottom side opposing the top side, an inside peripheral edge, and an outside peripheral edge, the enclosure including two legs connected with a back portion, the enclosure adapted for resting on the shoulders of the person around the person's neck, the bottom side of the enclosure shaped to conform to a curvature of the person's shoulders, the top side of the enclosure having at least one diffusion port in fluid communication with an interior space of the enclosure;
- a control circuit fixed at least partially within the interior space of the enclosure and including a controller, at least one user interface traversing the enclosure, a power source, and a diffusion mechanism connecting a reservoir that is adapted to contain the liquid with the at least one diffusion port in fluid communication with the interior space of the enclosure;
- wherein the enclosure further includes a filling port traversing the enclosure and in fluid communication with the reservoir such that the reservoir is capable of receiving the liquid by way of the filling port of the enclosure;
- whereby with the enclosure resting on the person's shoulders, the at least one user interface may be actuated to activate the control circuit to diffuse the liquid through the at least one diffusion port proximate the person's face.

17. A device for diffusing a liquid proximate a face of a person having a neck and shoulders, the device comprising:
- a generally U-shaped enclosure having a top side, a bottom side opposing the top side, an inside peripheral edge, and an outside peripheral edge, the enclosure including two legs connected with a back portion, the enclosure adapted for resting on the shoulders of the person around the person's neck, the bottom side of the enclosure shaped to conform to a curvature of the person's shoulders, the top side of the enclosure having at least one diffusion port in fluid communication with an interior space of the enclosure;
- a control circuit fixed at least partially within the interior space of the enclosure and including a controller, at least one user interface traversing the enclosure, a power source, and a diffusion mechanism including an electrically heated vaporizer or an ultrasonic atomizer, the diffusion mechanism connecting a reservoir that is adapted to contain the liquid with the at least one diffusion port in fluid communication with the interior space of the enclosure;
- wherein the enclosure further includes a filling port traversing the enclosure and in fluid communication with the reservoir such that the reservoir is capable of receiving the liquid by way of the filling port of the enclosure;
- whereby with the enclosure resting on the person's shoulders, the at least one user interface may be actuated to activate the control circuit to diffuse the liquid through the at least one diffusion port proximate the person's face.

\* \* \* \* \*